(12) United States Patent
Tajmamet et al.

(10) Patent No.: US 8,871,700 B2
(45) Date of Patent: Oct. 28, 2014

(54) LIQUID CLEANING AND DISINFECTING COMPOSITIONS COMPRISING A ZINC SALT AND AMINE OXIDE

(71) Applicant: The Procter & Gamble Company, Cincinnati, OH (US)

(72) Inventors: Jamila Tajmamet, Brussels (BE); Jean-Luc Philippe Bettiol, Brussels (BE); Robby Renilde Francois Keuleers, Lippelo (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/901,910

(22) Filed: May 24, 2013

(65) Prior Publication Data

US 2013/0261038 A1   Oct. 3, 2013

Related U.S. Application Data

(63) Continuation of application No. 13/428,211, filed on Mar. 23, 2012, now Pat. No. 8,470,755.

(51) Int. Cl.
| | |
|---|---|
| *C11D 3/48* | (2006.01) |
| *C11D 1/75* | (2006.01) |
| *C11D 1/83* | (2006.01) |
| *A61K 8/27* | (2006.01) |
| *A61K 8/40* | (2006.01) |
| *C11D 3/12* | (2006.01) |
| *A61K 8/46* | (2006.01) |
| *A61Q 17/00* | (2006.01) |
| *A01N 25/30* | (2006.01) |
| *A01N 59/16* | (2006.01) |
| *C11D 3/04* | (2006.01) |

(52) U.S. Cl.
CPC .............. *C11D 3/1233* (2013.01); *A61K 8/27* (2013.01); *A61K 8/40* (2013.01); *A61K 8/463* (2013.01); *C11D 1/75* (2013.01); *A61Q 17/005* (2013.01); *A01N 25/30* (2013.01); *C11D 1/83* (2013.01); *A01N 59/16* (2013.01); *C11D 3/046* (2013.01); *C11D 3/48* (2013.01)
USPC ........... 510/237; 510/235; 510/382; 510/390; 510/421; 510/422; 510/426; 510/427; 510/432; 510/503

(58) Field of Classification Search
USPC ......... 510/235, 237, 382, 390, 421, 422, 426, 510/427, 432, 503
See application file for complete search history.

(56) References Cited

U.S. PATENT DOCUMENTS

| | | | |
|---|---|---|---|
| 3,336,387 A | 8/1967 | Finch et al. | |
| 3,842,847 A * | 10/1974 | Hewitt et al. | 132/202 |
| 4,033,895 A | 7/1977 | Gerstein | |
| 4,229,313 A | 10/1980 | Joy | |
| 4,576,728 A | 3/1986 | Stoddart | |
| 4,783,283 A | 11/1988 | Stoddart | |
| 5,085,744 A | 2/1992 | Brasch | |
| 5,476,615 A | 12/1995 | Hall et al. | |
| 5,484,555 A | 1/1996 | Schepers | |
| 5,679,633 A | 10/1997 | Tseng | |
| 5,972,875 A | 10/1999 | Crutcher et al. | |
| 6,015,547 A | 1/2000 | Yam | |
| 6,034,043 A | 3/2000 | Fujiwara et al. | |
| 6,043,204 A * | 3/2000 | Kaufman et al. | 510/130 |
| 6,046,146 A | 4/2000 | Erilli | |
| 6,255,270 B1 | 7/2001 | Barger et al. | |
| 6,454,813 B1 | 9/2002 | Chan | |
| 6,482,788 B1 | 11/2002 | Arvanitidou | |
| 6,492,313 B1 | 12/2002 | Connors et al. | |
| 6,492,513 B1 | 12/2002 | Nishihara et al. | |
| 6,495,500 B1 * | 12/2002 | Connors et al. | 510/221 |
| 6,506,261 B1 | 1/2003 | Man | |
| 6,544,940 B1 | 4/2003 | Arvanitidou | |
| 6,617,293 B2 | 9/2003 | Chen | |
| 6,617,296 B1 | 9/2003 | Connors et al. | |
| 6,762,157 B1 | 7/2004 | Babinski et al. | |
| 7,196,045 B2 | 3/2007 | Lentsch et al. | |
| 7,452,853 B2 | 11/2008 | Smith et al. | |
| 7,465,697 B1 | 12/2008 | DeAth | |
| 7,524,803 B2 | 4/2009 | Lentsch et al. | |
| 7,829,516 B2 | 11/2010 | Smith et al. | |
| 2003/0199402 A1 | 10/2003 | Triplett et al. | |
| 2004/0204331 A1 | 10/2004 | Connors et al. | |
| 2005/0003979 A1 | 1/2005 | Lentsch et al. | |
| 2005/0020464 A1 | 1/2005 | Smith et al. | |

(Continued)

FOREIGN PATENT DOCUMENTS

| | | |
|---|---|---|
| DE | 102005025332 A1 | 12/2006 |
| DE | 102007008655 A1 | 8/2008 |
| EP | 0 079 697 A1 | 5/1983 |
| EP | 0 129 980 A2 | 1/1985 |
| EP | 0 137 871 A1 | 4/1985 |
| EP | 0 274 885 A1 | 7/1988 |
| JP | 2001172697 A | 6/2001 |
| JP | 4024446 B2 | 12/2007 |
| JP | 2008 156590 A | 7/2008 |
| JP | 2008156590 * | 7/2008 |
| JP | 4230203 B2 | 2/2009 |
| JP | 4252293 B2 | 4/2009 |
| WO | WO 97/06237 A1 | 2/1997 |
| WO | WO 97/23594 A1 | 7/1997 |
| WO | WO 2008/043638 A1 | 4/2008 |
| WO | WO 2008/052303 A1 | 5/2008 |
| WO | WO 2009/143516 A1 | 11/2009 |

OTHER PUBLICATIONS

U.S. Appl. No. 13/428,235, filed Mar. 23, 2012, Tajmamet, et al.
International Search Report; International Application No. PCT/US2013/032924; date of mailing Jun. 14, 2013; 6 pages.
International Search Report; International Application No. PCT/US2013/032926; date of mailing Jun. 14, 2013; 5 pages.
WPI World Patent Information Derwent, XP002086145; vol. 40, No. 82; Feb. 20, 1981; abstract.

*Primary Examiner* — Charles Boyer
(74) *Attorney, Agent, or Firm* — Amy I Ahn-Roll; John T Dipre

(57) ABSTRACT

The present invention relates to cleaning and disinfecting liquid detergent compositions and, in one embodiment, liquid hand dishwashing compositions, comprising a metal salt, preferably a divalent metal salt, preferably $Zn^{2+}$-salt and linear alkyl nucleophilic surfactant, preferably a linear alkyl chain amine oxide.
The present invention further relates to methods of disinfecting dishware and/or dishwashing implements and/or skin using such a liquid detergent compositions.

7 Claims, No Drawings

(56) References Cited

U.S. PATENT DOCUMENTS

| | | |
|---|---|---|
| 2005/0079983 A1 | 4/2005 | Paye |
| 2006/0105936 A1 | 5/2006 | Shi et al. |
| 2006/0128602 A1 | 6/2006 | Lentsch et al. |
| 2006/0264349 A1 | 11/2006 | Connors et al. |
| 2007/0054824 A1 | 3/2007 | Hahn |
| 2007/0111924 A1 | 5/2007 | Ford |
| 2007/0149431 A1 | 6/2007 | Lentsch et al. |
| 2008/0023031 A1 | 1/2008 | Kellar et al. |
| 2008/0275113 A1* | 11/2008 | Huetter et al. ............ 514/494 |
| 2009/0028961 A1 | 1/2009 | Lisowsky et al. |
| 2010/0132741 A1 | 6/2010 | Frey et al. |
| 2010/0160202 A1 | 6/2010 | Housmekerides et al. |
| 2010/0197548 A1 | 8/2010 | Bettiol et al. |
| 2010/0256035 A1* | 10/2010 | Konishi et al. ............ 510/218 |
| 2011/0171155 A1 | 7/2011 | Federle et al. |
| 2012/0035092 A1 | 2/2012 | Drehs et al. |
| 2012/0225943 A1 | 9/2012 | Gohl et al. |
| 2012/0227766 A1 | 9/2012 | Hafer et al. |
| 2012/0258900 A1* | 10/2012 | Adams et al. ............. 510/226 |

* cited by examiner

LIQUID CLEANING AND DISINFECTING COMPOSITIONS COMPRISING A ZINC SALT AND AMINE OXIDE

FIELD OF INVENTION

The present invention relates to liquid cleaning and disinfecting compositions and, in one embodiment, antibacterial liquid hand dishwashing compositions, comprising a metal salt and a linear alkyl nucleophilic surfactant, such as linear alkyl chain amine oxide. In one embodiment, the metal salt can be a divalent metal salt, preferably $Zn^{2+}$-salt.

BACKGROUND OF THE INVENTION

The cleaning and disinfecting of hard surfaces is important in both residential and commercial settings. The increasing importance of hygiene combined with the fast moving pace of the modern world has created a need for antibacterial products with fast cleaning and disinfecting action. The main concerns are to effectively reduce bacteria and maintain a consumer acceptable aesthetics profile while producing an acceptable human and environmentally safe composition. As will be appreciated, this implicitly puts constraints on the amount and type of chemicals that can be used to formulate a commercially acceptable composition.

As such, there remains a need for a cleaning and disinfecting product with a much more efficient antibacterial system that also maintains a consumer acceptable aesthetics profile while producing an acceptable human and environmentally safe composition.

It has surprisingly been found that when combining a metal salt, preferably a divalent metal salt, and, in one embodiment, $Zn^{2+}$-salt, with a linear alkyl nucleophilic surfactant with antibacterial activity, such as linear alkyl amine oxide, an unexpected antibacterial killing efficiency boost to the linear alkyl nucleophilic surfactant has been observed as compared to when the linear alkyl nucleophilic surfactant is formulated alone. As such, the intrinsic antibacterial efficacy of linear nucleophilic surfactants, such as linear alkyl amine oxide, is further leveraged and the need for further antibacterial technologies is limited, minimizing the impact on product aesthetics and human and environmental safety profile accordingly.

SUMMARY OF THE INVENTION

The present invention provides improvements in liquid cleaning and disinfecting compositions and in one embodiment liquid antibacterial dishwashing detergent compositions.

In one embodiment, a liquid cleaning and disinfecting composition comprises a linear alkyl nucleophilic surfactant and a metal salt. The linear alkyl nucleophilic surfactant is selected from the group of consisting of an anionic surfactant, a zwitterionic surfactant, an amphoteric surfactant, semi-polar surfactant, and mixtures thereof.

In another embodiment, a liquid cleaning and disinfecting composition comprises a linear alkyl nucleophilic surfactant and a metal-salt. The linear alkyl nucleophilic surfactant is selected from the group of consisting of an anionic surfactant, a zwitterionic surfactant, an amphoteric surfactant, semi-polar surfactant, and mixtures thereof. The ratio of linear alkyl nucleophilic surfactant to the metal ion is between about 10 to about 300.

In yet another embodiment of the present invention, the liquid cleaning and disinfecting composition comprises a linear alkyl amine oxide and a metal-salt. The combined linear alkyl amine oxide and metal salt provides an improved antibacterial efficacy versus when testing the linear alkyl amine oxide alone, in accordance with the ASTM E2149 shake flask method.

The present invention further relates to methods of cleaning and disinfecting hard and soft surfaces, such as dishware and dishwashing adjacencies, and laundry with improved cleaning and disinfecting liquid detergent compositions.

DETAILED DESCRIPTION OF THE INVENTION

The present invention relates to liquid cleaning and disinfecting compositions and, in one embodiment, antibacterial liquid hand dishwashing compositions, comprising a metal salt and a linear alkyl nucleophilic surfactant, such as linear alkyl chain amine oxide. In one embodiment, the metal salt can be a divalent metal salt, preferably $Zn^{2+}$-salt.

As used herein "grease" means materials comprising at least in part (i.e., at least 0.5 wt % by weight of the grease) saturated and unsaturated fats and oils, preferably oils and fats derived from animal sources such as beef and/or chicken.

As used herein "suds profile" means the amount of sudsing (high or low) and the persistence of sudsing (sustained sudsing) throughout the washing process resulting from the use of the liquid detergent composition of the present composition. As used herein "high sudsing" refers to liquid hand dishwashing detergent compositions which are both high sudsing (i.e. a level of sudsing considered acceptable to the consumer) and have sustained sudsing (i.e. a high level of sudsing maintained throughout the dishwashing operation). This is particularly important with respect to liquid dishwashing detergent compositions as the consumer uses high sudsing as an indicator of the performance of the detergent composition. Moreover, the consumer of a liquid dishwashing detergent composition also uses the sudsing profile as an indicator that the wash solution still contains active detergent ingredients. The consumer usually renews the wash solution when the sudsing subsides. Thus, a low sudsing liquid dishwashing detergent composition formulation will tend to be replaced by the consumer more frequently than is necessary because of the low sudsing level.

As used herein "dishware" means a surface such as dishes, glasses, pots, pans, baking dishes and flatware made from ceramic, china, metal, glass, plastic (polyethylene, polypropylene, polystyrene, etc.) and wood.

As used herein "dishwashing cleaning device or implement" means physical tools to be applied by the consumer during the dishwashing process to get the soil physically removed from the dishware, including but not limited to cloths, sponges and brushes.

As used herein "liquid detergent compositions" means liquid hand dishwashing detergent compositions, heavy duty liquid laundry detergent compositions and liquid hard surface detergent compositions.

As used herein "liquid hand dishwashing detergent composition" refers to those compositions that are employed in manual (i.e. hand) dishwashing. Such compositions are generally high sudsing or foaming in nature.

As used herein "cleaning" means applying to a surface for the purpose of cleaning, and/or disinfecting.

The Liquid Composition

The liquid cleaning compositions herein typically include a liquid composition containing from 30% to 95%, preferably from 40% to 90%, more preferably from 50% to 85% by weight of a liquid carrier in which the other essential and optional compositions components are dissolved, dispersed or suspended. One preferred component of the liquid carrier is water.

The liquid cleaning composition herein may have any suitable pH. Preferably the pH of the composition is adjusted to between 3 and 14, more preferably between 4 and 13, more preferably between 6 and 12 most preferably between 8 and 10. The pH of the composition can be adjusted using pH modifying ingredients known in the art.

The liquid cleaning compositions of the present invention can be in the form of liquid, semi-liquid, cream, lotion or gel compositions and, in some embodiments, are intended for use as liquid hand dishwashing detergent compositions for direct or indirect application onto dishware.

These compositions include single phase Newtonian or non-Newtonian products with a high shear viscosity of between about 100 cps and 10000 cps at 20° C. and, alternatively, between about 300 cps and about 8000 cps, between about 500 cps and about 5000 cps, between about 700 cps and about 3000 cps, between 900 and 2000 cps, between 1000 and 1500 cps. Alternatively the disinfecting product could imply multi-phase products containing at least one visually distinct phase and, alternatively, 2, 3, 4, 5 or more phases, preferably having a high shear viscosity of between about 100 cps and 10000 cps at 20° C. and, alternatively, between about 300 cps and about 8000 cps, between, 500 cps and 5000 cps, between about 700 cps and about 3000 cps, between about 900 cps and about 2000 cps, between 1000 and 1500 cps, and a low shear viscosity of between about 10,000 cps and about 250,000 cps at 20° C., and, alternatively, between about 40,000 cps and about 150,000 cps, between about 50,000 cps and about 80,000 cps and about 60,000 cps and about 70,000 cps.

In one preferred embodiment, the rheology may be achieved through the use of internal structurants. In one embodiment, the internal structurants are created through the use of an aqueous surfactant mesophase or a dispersion of a mesophase in a continuous aqueous medium. Suitable surfactant mesophases can include dispersed lamellar, spherulitic and expanded lamellar phases. In yet another embodiment, the internally structured liquid can be obtained by mixing a surfactant with any non-surfactant active capable of interacting with the surfactant to form or enhance (e.g. increase the yield point of) a structured system. This non-surfactant active typically is a surfactant de-solubilizer, typically an electrolyte. In another preferred embodiment, the rheology may be achieved through the use of external structurants, such as crystalline structurants including but not limited to microfibrous cellulose, crystalline hydroxyl-containing fatty acids, fatty esters or fatty waxes such as hydrogenated castor oil derivatives, amido-gellants and clays, non-crystalline structuring polymers including naturally or synthetic derived polymeric structurants, and mixtures thereof. In still another preferred embodiment, the rheology may be achieved by employing combinations of external and internal structurants. Multiphase products could be desired when aiming at distributing incompatible or reactive materials amongst the multiple liquid phases, such that the chemical and/or physical stability of the materials is maintained, to prevent problems with physical separation of the materials, or a desired active is generated upon use. Furthermore, the compositions of the present invention could encompass isotropic or non lamellar phase, lamellar phases or mixtures thereof.

The composition can also have a yield stress value of from about 0.003 Pa to about 5.0 Pa at about 20° C. and, alternatively, from about 0.01 Pa to about 3.0 Pa, from about 0.1 Pa to about 2.0 Pa and from about 0.5 Pa to about 1.0 Pa, as such being enabled to suspend material.

Essential materials for the present invention include both linear alkyl nucleophilic surfactants, preferably linear alkyl amine oxides and metal ions, preferably divalent metal-ion and, in one embodiment, $Zn^{2+}$-ions. Preferably, the linear alkyl nucleophilic surfactants, such as linear alkyl amine oxide, is present versus the divalent metal-ion, such as $Zn^{2+}$ ions, at a ratio of 10 to 300, preferably 15 to 200, more preferably 20 to 150, and most preferably 25 to 100.

Linear Alkyl Nucleophilic Surfactants:

An essential material for the current liquid cleaning compositions is the use of a linear alkyl nucleophilic surfactant. In one embodiment, the linear alkyl carbon chain comprises between 8 and 18 carbon atoms and can be substituted by a nucleophilic head group. This nucleophilic head group can comprise a free electron pair and a (partial) negative charge allowing it to complex with the positively charged metal ion. Nucleophilic head groups can include negatively charged head groups such as carboxylates, sulfates, sulfonates or phosphates. Also included can be zwitterionic or amphoteric head groups including betain and sulfobetain hydrophilic groups, as well as semi-polar hydrophilic head groups, such as amine oxides. In one preferred embodiment, the linear alkyl nucleophilic surfactant is a linear alkyl amine oxide, which is described in more detail below. It will be understood, however, that while linear alkyl amine oxide will be described in more detail below, the description could equally apply to any linear alkyl nucleophilic surfactant.

Amine Oxides:

Amine oxides are widely used in cleaning formulations to provide high levels of suds formation and grease cleaning efficacy. Most frequently used amine oxides are alkyl dimethyl amine oxide or alkyl amido propyl dimethyl amine oxide and derivatives thereof. Amine oxide may have linear, symmetrically or asymmetrically branched alkyl moieties.

Most preferred amine oxides for the present invention are linear alkyl amine oxides. Typical linear alkyl amine oxides include water-soluble amine oxides of the formula R1-N(R2)(R3)O and contain one R1 $C_{8-18}$ alkyl moiety and 2 R2 and R3 moieties typically selected from the group consisting of hydrogen, $C_{1-3}$ alkyl groups and $C_{1-3}$ hydroxyalkyl groups. Preferably, $R_1$ is a $C_{8-18}$ alkyl and $R_2$ and $R_3$ are typically selected from the group consisting of hydrogen, methyl, ethyl, propyl, isopropyl, 2-hydroxethyl, 2-hydroxypropyl and 3-hydroxypropyl. The linear amine oxide surfactants in particular may include linear $C_{10}$-$C_{18}$ alkyl dimethyl amine oxides and linear $C_8$-$C_{12}$ alkoxy ethyl dihydroxy ethyl amine oxides. Preferred amine oxides include linear $C_{10}$, linear $C_{10}$-$C_{12}$, and linear $C_{12}$-$C_{14}$ alkyl dimethyl amine oxides.

Less preferred for this application are branched alkyl amine oxides. Despite these materials displaying some antibacterial efficacy, limited and, in some embodiments, no antibacterial efficacy boost has been found when formulating together with a metal ion including divalent ion including divalent Zn-ion. As used herein "symmetrically-branched" means that the amine oxide has one alkyl moiety having $n_1$ carbon atoms with one alkyl branch on the alkyl moiety having $n_2$ carbon atoms. The alkyl branch is located on the α or β carbon from the nitrogen on the alkyl moiety. This type of branching for the amine oxide is also known in the art as an internal amine oxide. The total sum of $n_1$ and $n_2$ is from 10 to 24 carbon atoms, preferably from 12 to 20, and more preferably from 10 to 16. The number of carbon atoms for the one alkyl moiety ($n_1$) should be approximately the same number of carbon atoms as the one alkyl branch ($n_2$) such that the one alkyl moiety and the one alkyl branch are symmetric. As used herein "symmetric" means that $|n_1-n_2|$ is less than or equal to 5, preferably 4, most preferably from 0 to 4 carbon atoms in at least 50 wt %, more preferably at least 75 wt % to 100 wt % of the symmetrically-branched amine oxides for use herein. When $|n_1-n_2|$ is greater than 5 the amine oxide is asymmetrically branched. The amine oxide further comprises two moieties, independently selected from a $C_{1-3}$ alkyl, a $C_{1-3}$ hydroxyalkyl group, or a polyethylene oxide group containing an average of from about 1 to about 3 ethylene oxide groups. Preferably the two moieties are selected from a $C_{1-3}$ alkyl, more preferably both are selected as a $C_1$ alkyl.

When formulating linear alkyl amine oxides together with a metal ion, preferably a divalent metal ion, most preferably divalent Zn-ion, an improved antibacterial efficacy has been found versus when formulating the linear alkyl amine oxide alone. This improved antibacterial effect has not been observed when introducing sterical or packing hindrance inside the alkyl chain through alkyl or alkyl derivative branches or through introduction of spacing groups inside of the alkyl chain, such as amidoalkyl including amidopropyl units. Without wishing to be bound by theory, it is believed that the absence of sterical hindrance in the linear alkyl chain provides for efficient packing of amine oxide molecules around both the metal ion and at the bacterial membrane interface. Specifically, without wishing to be bound by theory, it is believed that the $Zn^{2+}$ molecules interact with both the amine oxide and bacterial wall, thereby acting as a deposition aid by binding the amine oxide to the bacterial wall and, as such, maximizing the antibacterial efficacy of the amine oxide.

Metal Ions:

Another essential material for use in the present liquid cleaning compositions are metal ions. The liquid cleaning compositions of the present invention can comprise metal ions at a level of 0.001% to 10%, preferably 0.01% to 1%, and more preferably 0.05% to 0.5%, by weight of the liquid cleaning composition. In a preferred embodiment, the composition may comprise metal ions at a level of 0.1% to 0.2%.

In one preferred embodiment, the metal ions can be multivalent metal ions, preferably divalent metal ions. Non-limiting examples include heavy metal derivatives (organic and inorganic salts) of $Pb^{2+}$, $Zn^{2+}$, $Cu^{2+}$, Mercury and Tin compounds. In one embodiment, typical ions known in the art as water hardeners, such as Mg and Ca, are not included within the present invention. Examples of suitable $Zn^{2+}$ salts include but are not limited to Zn carbonate, Zn citrate, Zn acetate, Zn gluconate, Zn glycinate, Zn oxide, Zn hydroxide, Zn sulfate, zinc bacitracin, zinc benzoate, zinc borate, zinc bromate, zinc bromide, zinc chlorate, zinc chloride, Zn iodide, Zn fluoride, zinc ethysulfate, zinc fluorosilicate, zinc formate, zinc hydrosulfite, zinc hydroxide, zinc lactate, zinc laurate, zinc linoleate, zinc malate, zinc nitrate, zinc perborate, zinc phosphate, zinc salicylate, zinc silicate, zinc stearate, zinc sulfamate, zinc sulfide, zinc sulfite and zinc tartrate, and mixtures thereof. In one preferred embodiment, the divalent metal ions are divalent Zn compounds especially Zn carbonate, Zn sulfate and Zn citrate compounds, and mixtures thereof. Preferably, it has been found that these metal ions do not directly contribute to the antibacterial activity of the composition, but, rather, act as a deposition aid to maximize the antibacterial activity of the linear alkyl nucleophilic surfactant, which can nucleophilically bind to the metal ion.

A more detailed description of other typical and optional materials formulated in detergent compositions including hand dishwashing detergent compositions is given below.

Surfactants:

The liquid cleaning compositions of the present invention may comprise an aqueous cleaning phase that may contain a surfactant suitable for application to dishware or other hard surfaces, skin or fabrics. Suitable surfactants for use herein include any known or otherwise effective cleansing surfactant suitable for application to hard surfaces or a user's skin, and which is otherwise compatible with the other essential ingredients in the aqueous cleansing phase of the compositions. These cleansing surfactants may include anionic, nonionic, cationic, zwitterionic or amphoteric surfactants, or combinations thereof.

The aqueous cleansing phase of the liquid cleaning composition comprises surfactant at concentrations ranging from about 1 to about 50%, more preferably from about 5 to about 45%, even more preferably from about 8 to 40%, even more preferably from about 12 to 35% by weight of the liquid detergent composition. In one embodiment of the present invention, the surfactant concentrations ranges from about 1 to about 40%, preferably from about 6 to about 32%, more preferably from about 8 to about 25% weight of the total composition of an anionic surfactant combined with about 0.01 to about 20%, preferably from about 0.2 to about 15%, more preferably from about 0.5 to about 10% by weight of the liquid detergent composition of amphoteric and/or zwitterionic and/or nonionic and/or cationic surfactant, more preferably an amphoteric or zwitterionic and even more preferred an amine oxide surfactant or betaine surfactant, even more preferred an amine oxide surfactant, most preferred a linear alkyl amine oxide when formulated together with a divalent metal ion such as divalent Zn-ion.

Non-limiting examples of optional surfactants are discussed below.

Anionic Surfactant

In one embodiment of the present invention, the cleaning phase of the present invention will comprise an anionic surfactant typically at a level of 1% to 40%, preferably 6% to 32%, more preferably 8% to 25% weight of the liquid detergent composition. In a preferred embodiment the composition has no more than 15%, preferably no more than 10%, more preferably no more than 5% by weight of the total composition, of a sulfonate surfactant.

Suitable anionic surfactants to be used in the compositions and methods of the present invention are sulfate, sulfonate, sulfosuccinates and/or sulfoacetate; preferably alkyl sulfate and/or alkyl ethoxy sulfates; more preferably a combination of alkyl sulfates and/or alkyl ethoxy sulfates with a combined ethoxylation degree less than 5, preferably less than 3, more preferably less than 2.

Sulphate Surfactants

Suitable sulphate surfactants may include water-soluble salts or acids of $C_{10}$-$C_{14}$ alkyl or hydroxyalkyl, sulphate and/or ether sulfate. Suitable counterions include hydrogen, alkali metal cation or ammonium or substituted ammonium, but preferably sodium.

The hydrocarbyl chain might be linear or branched. Where the hydrocarbyl chain is branched, it preferably comprises $C_{1-4}$ alkyl branching units. Mixtures of anionic surfactants with different branching levels on the hydrocarbyl group might be applied. The average percentage branching of such a mixture of the sulphate surfactants is preferably greater than 20%, more preferably greater than 30%, more preferably from 35% to 80% and most preferably from 40% to 60% of the total hydrocarbyl chains.

The sulphate surfactants may be selected from $C_8$-$C_{20}$ primary, branched-chain and random alkyl sulphates (AS); $C_{10}$-$C_{18}$ secondary (2,3) alkyl sulphates; $C_{10}$-$C_{18}$ alkyl alkoxy sulphates ($AE_xS$) wherein preferably x is from 1-30; $C_{10}$-$C_{18}$ alkyl alkoxy carboxylates preferably comprising 1-5 ethoxy units; mid-chain branched alkyl sulphates as discussed in U.S. Pat. Nos. 6,020,303 and 6,060,443; mid-chain branched alkyl alkoxy sulphates as discussed in U.S. Pat. Nos. 6,008,181 and 6,020,303.

Alkyl Sulfosuccinates—Sulfoacetate:

Other suitable anionic surfactants are alkyl, preferably dialkyl, sulfosuccinates and/or sulfoacetate. The dialkyl sulfosuccinates may be a $C_{6-15}$ linear or branched dialkyl sulfosuccinate. The alkyl moieties may be asymmetrical (i.e., different alkyl moiety.es) or preferably symmetrical (i.e., the same alkyl moieties).

Sulphonate Surfactants:

The compositions of the present invention may preferably comprise no more than 15% by weight, preferably no more than 10%, even more preferably no more than 5% by weight of the liquid detergent composition, of a sulphonate surfactant. Those include water-soluble salts or acids of $C_{10}$-$C_{14}$ alkyl or hydroxyalkyl, sulphonates; $C_{11}$-$C_{18}$ alkyl benzene sulphonates (LAS), modified alkylbenzene sulphonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulphonate (MES); and alpha-olefin sulphonate (AOS). Those also include the paraffin sulphonates may be monosulphonates and/or disulphonates, obtained by sulphonating paraffins of 10 to 20 carbon atoms. The sulfonate surfactant also include the alkyl glyceryl sulphonate surfactants. Sulphonated hydrotropes such as cumene sulphonate, toluene sulphonate and xylene sulphonate are not considered as sulphonated surfactants in this application.

Further Surfactants

The compositions can further comprise a surfactant selected from nonionic, cationic, amphoteric, zwitterionic, semi-polar nonionic surfactants, and mixtures thereof. In a further preferred embodiment, the composition of the present invention can further comprise amphoteric and/or zwitterionic surfactant, more preferably an amine oxide or betaine surfactant, even more preferably an amine oxide, most preferably a linear alkyl amine oxide when formulated together with metal ions including divalent Zn-ions.

The most preferred surfactant system for the compositions of the present invention can therefore comprise: (i) 1% to 40%, preferably 6% to 32%, more preferably 8% to 25% weight of the total composition of an anionic surfactant (2) combined with 0.01% to 20% wt, preferably from 0.2% to 15% wt, more preferably from 0.5% to 10% by weight of the liquid detergent composition of an amphoteric and/or zwitterionic and/or nonionic surfactant, more preferably an amphoteric and even more preferred an amine oxide surfactant. It has been found that such surfactant system will provide the excellent cleaning required from a hand dishwashing liquid composition while being very soft and gentle to the hands. Beyond the amine oxide will also strongly contribute to the antibacterial efficacy of the disinfecting product.

The total level of surfactants is usually from about 1 to about 50%, more preferably from about 5 to about 45%, even more preferably from about 8 to 40%, even more preferably from about 12 to 35% by weight of the liquid detergent composition.

Amphoteric and Zwitterionic Surfactants

The amphoteric and zwitterionic surfactant can be comprised at a level of from 0.01% to 20%, preferably from 0.2% to 15%, more preferably 0.5% to 10% by weight of the liquid detergent composition. Suitable amphoteric and zwitterionic surfactants are amine oxides and betaines.

Beyond the amine oxide surfactants already described before, other suitable amphoteric surfactants include betaines such alkyl betaines, alkylamidobetaine, amidazoliniumbetaine, sulfobetaine (INCI Sultaines) as well as the Phosphobetaine and preferably meets formula I:

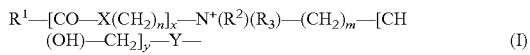

wherein
  $R^1$ is a saturated or unsaturated C6-22 alkyl residue, preferably C8-18 alkyl residue, in particular a saturated C10-16 alkyl residue, for example a saturated C12-14 alkyl residue;
  X is NH, $NR^4$ with C1-4 Alkyl residue $R^4$, O or S,
  n a number from 1 to 10, preferably 2 to 5, in particular 3,
  x 0 or 1, preferably 1,
  $R^2$, $R^3$ are independently a C1-4 alkyl residue, potentially hydroxy substituted such as a hydroxyethyl, preferably a methyl.
  m a number from 1 to 4, in particular 1, 2 or 3,
  y 0 or 1 and
  Y is COO, SO3, $OPO(OR^5)O$ or $P(O)(OR^5)O$, whereby $R^5$ is a hydrogen atom H or a Cl-4 alkyl residue.

Preferred betaines are the alkyl betaines of the formula (Ia), the alkyl amido betaine of the formula (Ib), the Sulfo betaines of the formula (Ic) and the Amido sulfobetaine of the formula (Id);

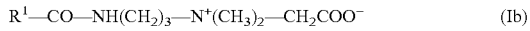

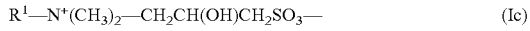

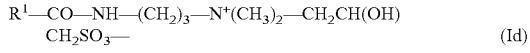

in which $R^1$ as the same meaning as in formula I. Particularly preferred betaines are the Carbobetaine [wherein $Y^-$=$COO^-$], in particular the Carbobetaine of the formula (Ia) and (Ib), more preferred are the Alkylamidobetaine of the formula (Ib).

Examples of suitable betaines and sulfobetaine are the following [designated in accordance with INCI]: Almondamidopropyl of betaines, Apricotam idopropyl betaines, Avocadamidopropyl of betaines, Babassuamidopropyl of betaines, Behenam idopropyl betaines, Behenyl of betaines, betaines, Canolam idopropyl betaines, Capryl/Capram idopropyl betaines, Carnitine, Cetyl of betaines, Cocamidoethyl of betaines, Cocam idopropyl betaines, Cocam idopropyl Hydroxysultaine, Coco betaines, Coco Hydroxysultaine, Coco/Oleam idopropyl betaines, Coco Sultaine, Decyl of betaines, Dihydroxyethyl Oleyl Glycinate, Dihydroxyethyl Soy Glycinate, Dihydroxyethyl Stearyl Glycinate, Dihydroxyethyl Tallow Glycinate, Dimethicone Propyl of PG-betaines, Erucam idopropyl Hydroxysultaine, Hydrogenated Tallow of betaines, Isostearam idopropyl betaines, Lauram idopropyl betaines, Lauryl of betaines, Lauryl Hydroxysultaine, Lauryl Sultaine, Milkam idopropyl betaines, Minkamidopropyl of betaines, Myristam idopropyl betaines, Myristyl of betaines, Oleam idopropyl betaines, Oleam idopropyl Hydroxysultaine, Oleyl of betaines, Olivamidopropyl of betaines, Palmam idopropyl betaines, Palm itam idopropyl betaines, Palmitoyl Carnitine, Palm Kernelam idopropyl betaines, Polytetrafluoroethylene Acetoxypropyl of betaines, Ricinoleam idopropyl betaines, Sesam idopropyl betaines, Soyam idopropyl betaines, Stearam idopropyl betaines, Stearyl of betaines, Tallowam idopropyl betaines, Tallowam idopropyl Hydroxysultaine, Tallow of betaines, Tallow Dihydroxyethyl of betaines, Undecylenam idopropyl betaines and Wheat Germam idopropyl betaines.

A preferred betaine is Cocoamidopropylbetain.

Nonionic Surfactants

Nonionic surfactant, when present, can comprise from 0.1% to 40%, preferably 0.2% to 20%, most preferably 0.5% to 10% by weight of the disinfecting liquid detergent composition. Suitable nonionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol.

Also suitable are alkylpolyglycosides having the formula $R^2O(C_nH_{2n}O)_t(glycosyl)_x$ (formula (III)), wherein $R^2$ of formula (III) is selected from the group consisting of alkyl, alkyl-phenyl, hydroxyalkyl, hydroxyalkylphenyl, and mixtures thereof in which the alkyl groups contain from 10 to 18, preferably from 12 to 14, carbon atoms; n of formula (III) is 2 or 3, preferably 2; t of formula (III) is from 0 to 10, preferably 0; and x of formula (III) is from 1.3 to 10, preferably from 1.3 to 3, most preferably from 1.3 to 2.7. The glycosyl is preferably derived from glucose. Also suitable are alkylglycerol ethers and sorbitan esters.

Also suitable are fatty acid amide surfactants having the formula (IV):

(IV)

wherein $R^6$ of formula (IV) is an alkyl group containing from 7 to 21, preferably from 9 to 17, carbon atoms and each $R^7$ of formula (IV) is selected from the group consisting of hydrogen, $C_1$-$C_4$ alkyl, $C_1$-$C_4$ hydroxyalkyl, and $-(C_2H_4O)_xH$ where x of formula (IV) varies from 1 to 3. Preferred amides are $C_8$-$C_{20}$ ammonia amides, monoethanolamides, diethanolamides, and isopropanolamides.

Cationic Surfactants

Cationic surfactants, when present in the composition for enhanced detergency effect, can be present in an effective amount, more preferably from 0.25% to 20%, by weight of the disinfecting liquid detergent composition. Suitable cationic surfactants are quaternary ammonium surfactants. Suitable quaternary ammonium surfactants are selected from the group consisting of mono $C_6$-$C_{16}$, preferably $C_6$-$C_{10}$ N-alkyl or alkenyl ammonium surfactants, wherein the remaining N positions are substituted by methyl, hydroxyethyl or hydroxypropyl groups. Other preferred cationic surfactants include alkyl benzalkonium halides and derivatives thereof, such as those available from Lonza under the BARQUAT and BARDAC tradenames. Another preferred cationic surfactant is an $C_6$-$C_{18}$ alkyl or alkenyl ester of a quaternary ammonium alcohol, such as quaternary chlorine esters. More preferably, the cationic surfactants have the formula (V):

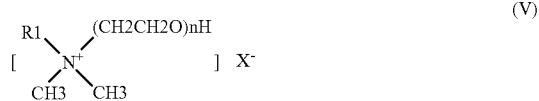

(V)

wherein R1 of formula (V) is $C_8$-$C_{18}$ hydrocarbyl and mixtures thereof, preferably, $C_{8-14}$ alkyl, more preferably, $C_8$, $C_{10}$ or $C_{12}$ alkyl, and X of formula (V) is an anion, preferably, chloride or bromide.

Sequestering Agent:

The liquid cleaning composition can preferably comprise sequestering agents, selected from the group but not limited to carboxylic acid based builders, chelants, or mixtures thereof. The sequestering agent or salt thereof, when present, can preferably present at the level of from 0.01% to 10%, more preferably from 0.1% to 5%, more preferably from 0.15% to 2.5%, more preferably from 0.2% to 1%, and most preferably from 0.25% to 0.5% by weight of the total composition.

Carboxylic Acid Based Builders:

In yet another embodiment of the present invention, the liquid cleaning compositions herein may optionally further comprise a linear or cyclic carboxylic acid, a polycarboxylic acid, or salt thereof. Beyond, the presence of anionic surfactants, especially when present in higher amounts in the region of 15-35% by weight of the total composition, results in the composition imparting a slippery feel to the hands of the user and the dishware. Carboxylic acids are also known to compensate for this.

Suitable (poly)carboxylic acids are acyclic, alicyclic, heterocyclic and aromatic carboxylic acids, in which case they contain at least two carboxyl groups which are in each case separated from one another by, preferably, no more than two carbon atoms. Polycarboxylates which comprise two carboxyl groups include, for example, water-soluble salts of malonic acid, (ethyl enedioxy) diacetic acid, maleic acid, diglycolic acid, tartaric acid, tartronic acid and fumaric acid. Carboxylic acids useful herein include $C_{1-6}$ linear or at least 3 carbon containing cyclic acids. The linear or cyclic carbon-containing chain of the carboxylic acid or salt thereof may be substituted with a substituent group selected from the group consisting of hydroxyl, ester, ether, aliphatic groups having from 1 to 6, more preferably 1 to 4 carbon atoms, and mixtures thereof.

Preferred carboxylic acids are those selected from the group consisting of salicylic acid, maleic acid, acetyl salicylic acid, 3 methyl salicylic acid, 4 hydroxy isophthalic acid, dihydroxyfumaric acid, 1,2, 4 benzene tricarboxylic acid, pentanoic acid and salts thereof, citric acid and salts thereof, and mixtures thereof. Where the carboxylic acid exists in the salt form, the cation of the salt is preferably selected from alkali metal, alkaline earth metal, monoethanolamine, diethanolamine or triethanolamine and mixtures thereof.

Other carboxylic acid based builders include homopolymers and copolymers of polycarboxylic acids and their partially or completely neutralized salts, monomeric polycarboxylic acids and hydroxycarboxylic acids and their salts. Another suitable polycarboxylic acid is the homopolymer of acrylic acid. Preferred salts of the above-mentioned compounds are the ammonium and/or alkali metal salts, i.e. the lithium, sodium, and potassium salts, and particularly preferred salts are the sodium salts. Preferred are also the polycarboxylates end capped with sulfonates.

Other carboxylate based chelants of potential interest include lactic acid, acetic acid, formic acid, succinic acid benzoic acid, salicylic acid and dehydroacetic acid all preferably in the form of a water-soluble salt.

Chelant:

In one embodiment of the present invention, the liquid cleaning compositions of the present invention may comprise a chelant.

As commonly understood in the detergent field, chelation herein means the binding or complexation of a bi- or multidentate ligand. These ligands, which are often organic compounds, are called chelants, chelators, chelating agents. Chelating agents form multiple bonds with a single metal ion. Chelants, are chemicals that form soluble, complex molecules with certain metal ions, inactivating the ions so that they cannot normally react with other elements or ions. The ligand forms a chelate complex with the substrate. The term is reserved for complexes in which the metal ion is bound to two or more atoms of the chelant. Chelants might also demonstrate crystal growth inhibition properties, i.e. those that interact with the small calcium and magnesium carbonate particles preventing them from aggregating into hard scale deposit. The particles repel each other and remain suspended in the water or form loose aggregates which may settle. These loose aggregates are easily rinsed away and do not form a deposit.

Suitable chelating agents can be selected from the group consisting of amino carboxylates, amino phosphonates, polyfunctionally-substituted aromatic chelating agents and mixtures thereof.

Preferred chelants for use herein are the amino acids based chelants and preferably glutamic-N,N-diacetic acid (GLDA) or methyl-glycine-diacetic acid (MGDA) and derivatives and/or Phosphonate based chelants and preferably Diethylenetriamine penta methylphosphonic acid (DTPMP) or hydroxyethyldiphosphonic acid (HEDP).

Amino carboxylates include ethylenediaminetetra-acetates, N-hydroxyethylethylenediaminetriacetates, nitrilotriacetates, ethylenediamine tetrapro-prionates, triethylenetetraaminehexacetates, diethylenetriaminepentaacetates, and ethanoldi-glycines, alkali metal, ammonium, and substituted ammonium salts therein and mixtures therein. As well as MGDA (methyl-glycine-diacetic acid), and salts and derivatives thereof and GLDA (glutamic-N,N-diacetic acid) and salts and derivatives thereof. GLDA (salts and derivatives thereof) is especially preferred according to the invention, with the tetrasodium salt thereof being especially preferred.

Other suitable chelants include amino acid based compound or a succinate based compound. The term "succinate based compound" and "succinic acid based compound" are used interchangeably herein. These include oxodisuccinates, carboxymethyloxysuccinate and mixtures of tartrate monosuccinic and tartrate disuccinic acid such as described in U.S. Pat. No. 4,663,071.

Other suitable chelants are described in U.S. Pat. No. 6,426,229. Particular suitable chelants include; for example, aspartic acid-N-monoacetic acid (ASMA), aspartic acid-N,N-diacetic acid (ASDA), aspartic acid-N-monopropionic acid (ASMP), iminodisuccinic acid (IDS), Imino diacetic acid (IDA), N-(2-sulfomethyl)aspartic acid (SMAS), N-(2-sulfoethyl)aspartic acid (SEAS), N-(2-sulfomethyl)glutamic acid (SMGL), N-(2-sulfoethyl)glutamic acid (SEGL), N-methyliminodiacetic acid (MIDA), alanine-N,N-diacetic acid (ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof. Also suitable is ethylenediamine disuccinate ("EDDS"), especially the [S,S] isomer as described in U.S. Pat. No. 4,704,233. Furthermore, Hydroxyethyleneiminodiacetic acid, Hydroxyiminodisuccinic acid, Hydroxyethylene diaminetriacetic acid are also suitable.

Amino phosphonates are also suitable for use as chelating agents and include ethylenediaminetetrakis (methylenephosphonates) as DEQUEST. Preferred, these amino phosphonates that do not contain alkyl or alkenyl groups with more than about 6 carbon atoms.

Polyfunctionally-substituted aromatic chelating agents are also useful in the compositions herein such as described in U.S. Pat. No. 3,812,044. Preferred compounds of this type in acid form are dihydroxydisulfobenzenes such as 1,2-dihydroxy-3,5-disulfobenzene.

Organic Solvents:

The liquid cleaning compositions of the present invention may comprise one or more organic solvents as a highly preferred optional ingredient.

Suitable solvents are selected from the group consisting of C4-14 preferably C6-C12 even more preferably C8-C10 ethers and diethers, glycols, alkoxylated glycols, $C_6$-$C_{16}$ glycol ethers, alkoxylated aromatic alcohols, aromatic alcohols, aliphatic branched alcohols, alkoxylated aliphatic branched alcohols, alkoxylated linear $C_1$-$C_5$ alcohols, linear $C_1$-$C_5$ alcohols, amines, $C_8$-$C_{14}$ alkyl and cycloalkyl hydrocarbons and halohydrocarbons, alkanolamines, terpenes and mixtures thereof.

Suitable glycols to be used herein are according to the formula HO—CR1R2-OH wherein R1 and R2 are independently H or a C2-C10 saturated or unsaturated aliphatic hydrocarbon chain and/or cyclic. Suitable glycols to be used herein are dodecaneglycol and/or propanediol, and derivatives thereof such as bronopol (2-bromo-2-nitropropane-1,3-diol).

Suitable alkoxylated glycols to be used herein are according to the formula R-(A)n-R1-OH wherein R is H, OH, a linear or branched, saturated or unsaturated alkyl of from 1 to 20 carbon atoms, preferably from 2 to 15 and more preferably from 2 to 10, wherein R1 is H or a linear saturated or unsaturated alkyl of from 1 to 20 carbon atoms, preferably from 2 to 15 and more preferably from 2 to 10, and A is an alkoxy group preferably ethoxy, methoxy, and/or propoxy and n is from 1 to 5, preferably 1 to 2. Suitable alkoxylated glycols to be used herein are methoxy octadecanol and/or ethoxyethoxyethanol.

Suitable alkoxylated aromatic alcohols to be used herein are according to the formula R-(A)n-OH wherein R is an alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated aromatic alcohols are benzoxyethanol and/or benzoxypropanol.

Suitable aromatic alcohols to be used herein are according to the formula R—OH wherein R is an alkyl substituted or non-alkyl substituted aryl group of from 1 to 20 carbon atoms, preferably from 1 to 15 and more preferably from 1 to 10. For example a suitable aromatic alcohol to be used herein is benzyl alcohol.

Suitable alkoxylated aliphatic alcohols to be used herein are according to the formula R-(A)n-OH wherein R is a linear or branched, saturated or unsaturated alkyl group of from 1 to 20 carbon atoms, preferably from 2 to 15 and more preferably from 3 to 12, wherein A is an alkoxy group preferably butoxy, propoxy and/or ethoxy, and n is an integer of from 1 to 5, preferably 1 to 2. Suitable alkoxylated aliphatic linear or branched alcohols are butoxy propoxy propanol (n-BPP), butoxyethanol, butoxypropanol (n-BP), ethoxyethanol, 1-methylpropoxyethanol, 2-methylbutoxyethanol, Hexyl glycol ether (Hexyl Cellosolve) and Hexyl diglycolether (HexylCarbitiol) or mixtures thereof. Butoxy propoxy propanol is commercially available under the trade name n-BPP® from Dow chemical. Butoxypropanol is commercially available from Dow chemical.

Suitable aliphatic alcohols to be used herein are according to the formula R—OH wherein R is a linear or branched, saturated or unsaturated alkyl group of from 1 to 20 carbon atoms, preferably from 2 to 15 and more preferably from 5 to 12. With the proviso that said aliphatic branched alcohols is not a 2-alkyl alkanol as described herein above. Suitable aliphatic alcohols are methanol, ethanol, propanol, isopropanol or mixtures thereof.

Suitable alkanolamines to be used herein include but are not limited to monoethanolamine, diethanolamine and triethanolamine.

Suitable terpenes to be used herein monocyclic terpenes, dicyclic terpenes and/or acyclic terpenes. Suitable terpenes are: D-limonene; pinene; pine oil; terpinene; terpene derivatives as menthol, terpineol, geraniol, thymol; and the citronella or citronellol types of ingredients.

Other suitable solvents include butyl diglycol ether (BDGE), hexandiols, butyltriglycol ether, teramilic alcohol and the like. BDGE is commercially available from Union Carbide or from BASF under the trade name Butyl CARBITOL®. Alternatively also diamines can be used. Specific examples of diamines are described further in the document in the other optional ingredients section.

Preferably said solvent is selected from the group consisting of butoxy propoxy propanol, butyl diglycol ether, benzyl alcohol, butoxypropanol, ethanol, methanol, isopropanol, hexandiols and mixtures thereof. More preferably said solvent is selected from the group consisting of butoxy propoxy propanol, benzyl alcohol, butoxypropanol, ethanol, methanol, isopropanol and mixtures thereof. Even more preferably said solvent is selected from the group consisting of benzyl alcohol, ethanol and mixtures thereof.

When present, the liquid cleaning composition may comprise from about 0.01% to about 25%, alternatively from about 0.5% to about 20%, alternatively from about 1% to about 15%, alternatively from 2% to 10%, alternatively 3 to 6% by weight of the liquid cleaning composition of said organic solvent. These organic solvents may be used in conjunction with water, or they may be used without water.

Alternatively hydrotropes might also be applied alone or in combination with any of the organic solvents mentioned above, to exhibit their solvent action, in an effective amount, i.e. from about 0.01% to about 25%, alternatively from about 0.5% to about 20%, alternatively from about 1% to about 15%, alternatively from 2% to 10%, alternatively 3 to 6% by weight of the liquid cleaning composition. Suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof, as disclosed in U.S. Pat. No. 3,915,903.

Antibacterial Actives:

In another embodiment of this present invention the liquid cleaning composition might also comprise one or more antibacterial agents to further boost the antibacterial efficacy. An antibacterial agent is a chemical substance or microorganism which can deter, render harmless, or exert a controlling effect on any harmful organism by chemical or biological means. The choice of antibacterial agent to be used depends on the particular situation. Some antibacterial agents have a wide spectrum (kill many different types of microorganisms), while others kill a smaller range of disease-causing organisms but are preferred for other properties (they may be non-corrosive, non-toxic, or inexpensive). Within Western Europe the antibacterial actives that can be used in detergent applications are classified within the "Biocidal Products Directive 98/8/EC (BPD")", more particularly within "MAIN GROUP 1: Disinfectants and general biocidal products—Product-type 2: Private area and public health area disinfectants and other biocidal products." Within North America antibacterial products and actives that can be used are regulated by the FDA and EPA. Potentially the antibacterial actives can be combined with antibacterial efficacy boosting technologies especially chelants, can be combined with an AB carrying agent to improve deposition efficacy, or could be bound to a deposition technology like a surface substantive deposition polymer to deliver a long lasting disinfection efficacy.

Typical chemistry classes with illustrating examples being used demonstrating intrinsic antibacterial activity include but are not limited to aldehydes (formaldehyde, glutaraldehyde, ortho-phtalaldehyde), sulphur dioxide, sulphites, bisulphites, vanillic acid esters), chlorine and oxygen based oxidizing agents (sodium and calcium hypochlorite or hypobromite, chloramine and chloramine-T, chlorine dioxide, hydrogen peroxide, iodine, ozone, peracetic acid, performic acid, potassium permanganate, potassium peroxymonosulfate), phenolics (phenol, o-phenylphenol, chloroxylenol, hexachlorophene, thymol, amylmetacresol, 2,4-dichlorobenzyl alcohol, policresylen, fentichlor, 4-allylcatechol, p-hydroxybenzoic acid esters including benzylparaben, butylparaben, ethylparaben, methtlparaben and propylparaben, butylated hydroxyanisole, butylated hydroxytoluene, capaicin, carvacrol, creosol, eugenol, guaiacol), halogenated (hydroxy) diphenylethers (diclosan, triclosan, hexachlorophene and bromochlorophene, 4-hexylresorcinol, 8-hydroxyquinoline and salts thereof), quaternary ammonium compounds (benzalkonium chloride derivatives, benzethonium chloride derivatives, cetrimonium chloride/bromide, cetylpyridinium, cetrimide, benzoxonium chloride, didecyldimethyl ammonium chloride), acridine derivatives (ethacridine lactate, 9-aminoacridine, euflavine), biguanides including polymeric biguanides, and amidines (polyaminopropyl biguanide, dibrompropamidine, chlorhexidine, alexidine, propamidine, hexamidine, polihexanide), nitrofuran derivatives (nitrofurazone), quinoline derivatives (dequalinium, chlorquinaldol, oxyquinoline, clioquinol), iodine products, essential oils (bay, cinnamon, clove, thyme, eucalyptus, peppermint, lemon, tea tree, magnolia extract, menthol, geraniol), cations, Anilides (saclicylanilide, Diphenylureas), salicylic acid esters including menthyl salicylate, methyl salicylate and phenyl salicylate, pyrocatechol, phtalic acid and salts thereof, hexetidine, octenidine, sanguinarine, domiphen bromide, alkylpyridinium chlorides such as cetylpyridinium chloride, tetradecylpyridinium chloride and N-tetradecyl-4-ethylpyridinium chloride, iodine, sulfonamides, piperidino derivatives such as delmopinol and octapinol, and mixtures thereof, miscellaneous preservatives (derivatives of 1,3-dioxane, derivatives of imidazole, Isothizolones, derivatives of hexamine, triazines, oxazolo-oxazoles, sodium hydroxymethylglycinate, methylene bisthiocyanate, captan).

The liquid cleaning composition may also contain a bleach or bleach system as disinfecting system, preferably a peroxide bleach, possibly in combinations with chelant, radical scavenger and specific surfactant system such as dodecyl dimethylamine oxide and derivatives to enable higher finished product pH, typically up to pH 9. More details are described in US Patent Pub. 2011/0152158. The peroxygen bleach component in the composition can also be formulated with an activator (peracid precursor). Possible activators include but are not limited to tetraacetyl ethylene diamine (TAED), benzoylcaprolactam and valerolactam derivatives, alkanoyloxybenzenesulphonate such as nonanoyloxybenzenesulphonate (NOBS), perhydrolyzable esters, and mixtures thereof. Further non-limiting list of examples, including quaternary substituted bleach activators, are described in U.S. Pat. No. 6,855,680. Alternatively organic peroxides such as diacylperoxides such as dibenzoyl peroxide can also be considered. Alternatively the composition might also comprise a bleach catalyst such as Metal-containing Bleach Catalysts preferably manganese and cobalt containing bleach catalysts, Transition Metal Complexes of Macropolycyclic Rigid Ligands, or Other Bleach Catalysts such as organic bleach catalysts such as zwitterionic bleach catalysts including aryliminium zwitterions, and cationic bleach catalysts. Alternatively the composition may also comprise a preformed peracid such as phtalimidio peroxycaproic acid (PAP) or percarboxylic or percarbonic or perimidic or peroxymonosulfuric acid, or a bleaching enzyme.

A more detailed bleach description is given in U.S. Application No. 61/512,150.

Preferred antibacterial systems are halogenated benzyl alcohol derivatives such as chloroxylenol (PCMX), halogenated hydroxydiphenylethers preferably diclosan, quaternary ammonium salts preferably alkylbenzalkonium and alkylbenzethonium chloride and derivatives thereof, essential oils, bleach system preferably a peroxide bleach, and mixtures thereof. Most preferred antibacterial systems are benzalkonium chloride, diclosan and PCMX.

Other Components:

The liquid cleaning composition herein can further comprise a number of other components such as, but not limited to, internal or external structuring systems, skin care actives including cationic conditioning polymers, humectants, emollients, enzymes and skin rejuvenation actives, polymers including cleaning or soil anti-redeposition polymers, surface modifying polymers and soil flocculating polymers, suspended particles including beads, cleaning and/or exfoliating particles, air bubbles, perfume microcapsules and pearlescent agents, perfume and malodor control compounds, colorants, organic and inorganic opacifiers, organic and inorganic cations such as alkaline earth metals such as Ca/Mg-ions and diamines, suds stabilizers/boosters, anti-caking agents, viscosity trimming agents (e.g. salt such as NaCl and other mono-, di- and trivalent salts), preservatives and pH trimming and/or buffering means (e.g. carboxylic acids such as citric acid, HCl, NaOH, KOH, amines and alkanolamines, phosphoric and sulfonic acids, carbonates such as sodium carbonates, bicarbonates, sesquicarbonates, borates, silicates, phosphates, imidazole and alike).

A more detailed description of these optional ingredients is given in U.S. Application No. 61/512,150.

Packaging:

The liquid cleaning compositions of the present invention may be packed in any suitable packaging for delivering the liquid disinfecting detergent composition for use. Preferably, the package is a transparent or translucent package made of glass or plastic so that consumers can see the product throughout the packaging.

The Process of Cleaning/Treating a Hard Surface

Another embodiment of the present invention is directed to a process of cleaning a hard surface, such as dishware, with a composition of the present invention. Said processes comprises the step of applying the composition onto the hard surface, such as dishware, typically in diluted or neat form and rinsing or leaving the composition to dry on the surface without rinsing the surface.

By "in its neat form", it is meant herein that said liquid composition is applied directly onto the surface to be treated and/or onto a cleaning device or implement such as a dish cloth, a sponge or a dish brush without undergoing any dilution at 0 gpg water hardness by the user (immediately) prior to the application. By "diluted form", it is meant herein that said liquid composition is diluted by the user with an appropriate solvent, typically water. By "rinsing", it is meant herein contacting the dishware cleaned with the process according to the present invention with substantial quantities of appropriate solvent, typically water, after the step of applying the liquid composition herein onto said dishware. By "substantial quantities", it is meant usually about 5 to about 20 liters.

In one embodiment of the present invention, the composition herein can be applied in its diluted form. Soiled dishes are contacted with an effective amount, typically from about 0.5 ml to about 20 ml (per about 25 dishes being treated), preferably from about 3 ml to about 10 ml, of the liquid detergent composition of the present invention diluted in water. The actual amount of liquid detergent composition used will be based on the judgment of user, and will typically depend upon factors such as the particular product formulation of the composition, including the concentration of active ingredients in the composition, the number of soiled dishes to be cleaned, the degree of soiling on the dishes, and the like. Generally, from about 0.01 ml to about 150 ml, preferably from about 3 ml to about 40 ml of a liquid detergent composition of the invention is combined with from about 2000 ml to about 20000 ml, more typically from about 5000 ml to about 15000 ml of water in a sink having a volumetric capacity in the range of from about 1000 ml to about 20000 ml, more typically from about 5000 ml to about 15000 ml. The soiled dishes are immersed in the sink containing the diluted compositions then obtained, where contacting the soiled surface of the dish with a cloth, sponge, or similar article cleans them. The cloth, sponge, or similar article may be immersed in the detergent composition and water mixture prior to being contacted with the dish surface, and is typically contacted with the dish surface for a period of time ranged from about 1 to about 10 seconds, although the actual time will vary with each application and user. The contacting of cloth, sponge, or similar article to the dish surface is preferably accompanied by a concurrent scrubbing of the dish surface.

Another method of the present invention will comprise immersing the soiled dishes into a water bath or held under running water without any liquid dishwashing detergent. A device for absorbing liquid dishwashing detergent, such as a sponge, is placed directly into a separate quantity of undiluted liquid dishwashing composition for a period of time typically ranging from about 1 to about 5 seconds. The absorbing device, and consequently the undiluted liquid dishwashing composition, is then contacted individually to the surface of each of the soiled dishes to remove said soiling. The absorbing device is typically contacted with each dish surface for a period of time range from about 1 to about 10 seconds, although the actual time of application will be dependent upon factors such as the degree of soiling of the dish. The contacting of the absorbing device to the dish surface is preferably accompanied by concurrent scrubbing.

Alternatively, the device may be immersed in a mixture of the hand dishwashing composition and water prior to being contacted with the dish surface, the concentrated solution is made by diluting the hand dishwashing composition with water in a small container that can accommodate the cleaning device at weight ratios ranging from about 95:5 to about 5:95, preferably about 80:20 to about 20:80 and more preferably about 70:30 to about 30:70, respectively, of hand dishwashing liquid:water respectively depending upon the user habits and the cleaning task.

Dependent on the geography of use of the composition, the water used in the method of the present invention can have a hardness level of about 0-30 gpg ("gpg" is a measure of water hardness that is well known to those skilled in the art, and it stands for "grains per gallon").

The Process of Treating a Cleaning Device or Implement

In one embodiment we also aim to disinfect cleaning devices or implements. More particularly the cleaning and disinfecting liquid is applied "in its neat form", directly onto a humid or dry cleaning device or implement such as a dish cloth, a sponge or a dish brush, and left without undergoing any substantial dilution (ie. more than the humidity already present in the cleaning device or implement prior to applying the disinfecting liquid) for about 30 seconds, preferably about 5 minutes up to about 24 hours, i.e. till the next dishwashing process is initiated.

The Process of Treating Skin or Hard Surfaces

In yet another embodiment, the liquid cleaning composition can applied to a user's skin or to hard surfaces, such as dishware, cutting boards and kitchen surfaces. More particularly the liquid cleaning composition is applied "in its neat or in its diluted form", directly or through an implement onto a humid or dry skin or a hard surface, such as a dishware or kitchen surfaces, left to act for about 30 seconds, preferably about 5 minutes up to about 24 hours, optionally followed by a rinsing step.

EXAMPLES

The below examples illustrate the improved antibacterial efficacy observed when formulating divalent ions, such as Zn2+-ions, together with linear alkyl amine oxide (table 1) versus when formulating divalent ions, such as Zn2+-ions, together with non-linear alkyl amine oxides. In particular, Table 2 illustrates the non-linear cocoamidopropyl dimethyl amine oxide and Tables 3 and 4 illustrate branched amine oxides.

The antibacterial efficacy was tested following the below Shake Flask protocol:

Materials:
  Microbial strains: *Staphylococcus aureus* (SA) CIP 4.83, *Escherichia Coli* (EC) CIP 53.126, *Pseudomonas Aeruginosa* (PA) CIP 82.113
  Culture media: TSA medium—Neutralizing medium (Dey Engley Broth)—Buffered Peptoned water (BPW-F)—Shake flask bottles—Physiological water
  Incubator Shake Flask Protocol: ASTM E2149 shake flask method
  Inoculum counting:
    For each strain, prepare an inoculum at 0.5 Mc Farland (McF). Dilute 1 ml of the inoculum with 9 ml of physiological water. Select 1 ml of the resulting dilution and dilute again with 9 ml of physiological water. Execute 5 dilution steps accordingly so that a $10^{-5}$ dilution is obtained.
    Recover 100 microliter of the $10^{-5}$ dilution and inoculate 2 petri dishes.
    Add 20 ml of TSA medium.
    Incubate at $32+/-0.5°$ C. during 24 hours
  Negative control:
    Put 5 ml of SA, EC or PA inoculums into a shake flask.
    Add 45 ml of pure BPW-F solution.
    Dilute twice in neutralizing medium: Recover 1 ml of the pure solution and add 9 ml of the neutralizing medium ($=10^{-1}$ and $10^{-2}$ dilution).
    Wait 5 minutes and put 100 microliter of the pure solution and the $10^{-2}$ dilution into 2 petri dishes, add 20 ml of TSA medium (T0).
    Do the same operation after 1 hour (T1h).
    Incubate at $32+/-0.5°$ C. during 24 hours
  Sample testing:
    Prepare a solution at a specified concentration (see data tables for actual concentrations as 100% active—final volume 50 ml). For example, for a 50% (V/V), dilute 25 ml of product with 20 ml of BPW-F and 5 ml of the inoculums (SA, EC or PA) at 0.5 McF.
    Dilute twice in neutralizing medium: Recover 1 ml of the pure solution and add 9 ml of the neutralizing medium ($=10^{-1}$ and $10^{-2}$ dilution).
    Wait 5 minutes and put 100 microliter of the pure solution and the $10^{-2}$ dilution into 2 petri dishes, add 20 ml of TSA medium (T0).
    Do the same operation after 1 hour (T1h).
    Incubate at $32+/-0.5°$ C. during 24 hours
  Calculation of log reduction:
    The log reduction is calculated as $\log(T0/T1h)$

TABLE 1

Improved antibacterial efficacy of Zn2+ (from zinc carbonate (ZnCO3)) together with linear C12-14 alkyl dimethyl amine oxide (AO) versus linear C12-14 alkyl dimethyl amine oxide (AO) alone.

| Log reduction (tested active concentration) | Zn2+ (58% active sol.) | Linear AO (32% active sol.) | Zn2+ and Linear AO (AO/ZnCO3 active ratio = 48) |
|---|---|---|---|
| E.coli | 0.17 (0.1%) | 0.41 (0.1%) | 2.03 (0.1%) |
| St. Aureus | 0.18 (0.1%) | 0.73 (0.1%) | 1.12 (0.1%) |
| Ps Aeroginosa | 0.27 (10%) | 2.10 (10%) | 3.07 (10%) |

As will be appreciated, the data in Table 1 illustrates that Zn2+ by itself does not directly contribute to the antibacterial activity of the composition.

TABLE 2

No antibacterial efficacy improvement of Zn2+ together with cocoamidopropyl dimethyl amine oxide (CAPAO) versus CAPAO alone.

| Log reduction (tested active concentration) | CAP AO (30.7% active sol.) | Zn 2+ and CAPAO (AO/ZnCO3 active ratio = 48) |
| --- | --- | --- |
| E.coli | 0.37 (1%) | 0.38 (1%) |
| St Aureus | 0.88 (1%) | 0.13 (1%) |
| Ps. aeroginosa | 1.3 (10%) | 0.06 (10%) |

TABLE 3

No antibacterial efficacy improvement of Zn2+ together with symmetrically branched dimethyl amine oxide versus symmetrically branched dimethyl amine oxide alone.

| Log reduction (tested active concentration) | Isalchem Mid Branched AO (34% active sol.) | Zn 2+ and Isalchem Mid Branched AO (AO/ZnCO3 active ratio = 48) |
| --- | --- | --- |
| E.Coli | 2.6 (0.1%) | 1.95 (0.1%) |
| Ps Aeroginosa | 3.29 (10%) | 3.22 (10%) |

TABLE 4

No Antibacterial efficacy improvement of Zn2+ together with methyl branched dimethyl amine oxide versus methyl branched dimethyl amine oxide alone.

| Log reduction (tested active concentration) | Shell type 1 Branched AO (N terminal) (32% active sol.) | Zn 2+ and Shell Type 1 AO (AO/ZnCO3 active ratio = 48) |
| --- | --- | --- |
| St. Aureus | 4.06 (0.1%) | 4.06 (0.1%) |
| Ps. aeroginosa | 3.98 (10%) | 4.61 (10%) |

TABLE 5

Representative hand dishwashing liquid formula examples of the present invention comprising a divalent Zn salt:

| % Ingredients (100% active) | Example 1 | Example 2 |
| --- | --- | --- |
| NaCl | 0.6 | 1.3 |
| Sodium citrate | 2 | 0 |
| PEI polymer | 0.5 | 0.25 |
| Polypropyleneglycol (MW2000) | 1.2 | 1.6 |
| Ethanol | 3.5 | 4 |
| Alkylethoxysulphate | 28 | 15 |
| Linear Amine Oxide | 7 | 5 |
| Zn-Carbonate* | 0.10* | 0.15* |
| Perfume, preservative and dye | Balance to 100 | Balance to 100 |

*- Percentage based on amount Zn ion present.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid cleaning and disinfecting composition comprising:
    a) from about 5 wt. % to about 20 wt. % C12-14 linear alkyl dimethyl amine oxide;
    b) from 0.1 wt. % to 0.2 wt. % of a Zn2+ salt selected from the group consisting of Zn carbonate, Zn sulphate, Zn citrate and mixtures thereof;
    c) from about 4 wt % to about 40 wt %, by weight of the total composition, of an anionic surfactant selected from the group consisting of alkyl sulfate, alkyl ethoxy sulfate and mixtures thereof;
    d) from about 0.01 wt % to about 4 wt %, by weight of the total composition, of an organic solvent selected from the group consisting of ethanol, benzyl alcohol, and mixtures thereof; and
    e) at least one biocide selected from the group consisting of a halogenated benzyl alcohol derivative, a halogenated hydroxydiphenylether, a quaternary ammonium salt, an alkylbenzethonium chloride, a peroxide bleach system, and mixtures thereof.

2. A liquid cleaning and disinfecting composition according to claim 1, further comprising from about 0.1% to about 20% by weight of the liquid detergent composition of a non-ionic surfactant selected from the group consisting of C8-C22 aliphatic alcohols with 1 to 25 moles of ethylene oxide, alkylpolyglycosides, fatty acid amide surfactants, and mixtures thereof.

3. A liquid cleaning and disinfecting composition according to claim 1 further comprising from about 0.01% to about 25%, by weight of the liquid detergent composition, of a hydrotrope selected from the group consisting of organic salts of cumene sulphonate, xylene sulphonate, toluene sulphonate, inorganic salts of cumene sulphonate, xylene sulphonate, toluene sulphonate, and mixtures thereof.

4. A liquid cleaning and disinfecting composition according to claim 1 further comprising from about 0.01% to about 10% by weight of the total composition of a sequestering agent selected from the group consisting of carboxylic acid based builders, amino carboxylate chelants, amino phosphonate chelants, polyfunctionally-substituted aromatic chelating agents and mixtures thereof.

5. A method of cleaning and disinfecting dishware and/or dishwashing implements and/or skin with a liquid cleaning and disinfecting composition according to claim 1, said method comprising the steps of applying the composition directly or indirectly onto the dishware and/or dishwashing implement and/or skin.

6. A liquid cleaning and disinfecting composition comprising:
    a) from about 5 wt. % to about 20 wt. % C12-14 linear alkyl dimethyl amine oxide;
    b) from 0.1 wt. % to 0.2 wt. % of a Zn2+ salt selected from the group consisting of Zn carbonate, Zn sulphate, Zn citrate and mixtures thereof;
    c) from about 4 wt % to about 40 wt %, by weight of the total composition, of an anionic surfactant selected from the group consisting of alkyl sulfate, alkyl ethoxy sulfate and mixtures thereof;
    d) from about 0.01 wt % to about 4 wt %, by weight of the total composition, of an organic solvent selected from the group consisting of ethanol, benzyl alcohol, and mixtures thereof; and
    e) at least one biocide selected from the group consisting of a halogenated benzyl alcohol derivative, a halogenated hydroxydiphenylether, a quaternary ammonium salt, an alkylbenzethonium chloride, a peroxide bleach system, and mixtures thereof;
    wherein the ratio of C12-14 linear alkyl dimethyl amine oxide to the Zn2+ salt is between about 10 to about 300.

7. A liquid cleaning and disinfecting composition comprising:
    a) from about 5 wt. % to about 20 wt. % C12-14 linear alkyl dimethyl amine oxide;
    b) from 0.1 wt. % to 0.2 wt. % of a Zn2+ salt selected from the group consisting of Zn carbonate, Zn sulphate, Zn citrate and mixtures thereof;
    c) from about 4 wt % to about 40 wt %, by weight of the total composition, of an anionic surfactant selected from the group consisting of alkyl sulfate, alkyl ethoxy sulfate and mixtures thereof;
    d) from about 0.01 wt % to about 4 wt %, by weight of the total composition, of an organic solvent selected from the group consisting of ethanol, benzyl alcohol, and mixtures thereof; and
    e) at least one biocide selected from the group consisting of a halogenated benzyl alcohol derivative, a halogenated hydroxydiphenylether, a quaternary ammonium salt, an alkylbenzethonium chloride, a peroxide bleach system, and mixtures thereof;
    wherein the combined C12-14 linear alkyl dimethyl amine oxide and Zn2+ salt provide an improved antibacterial efficacy versus when testing the C12-14 linear alkyl dimethyl amine oxide alone, in accordance with ASTM E2149 shake flask method.

* * * * *